United States Patent
Shih et al.

[11] Patent Number: 6,136,002
[45] Date of Patent: Oct. 24, 2000

[54] ANTERIOR SPINAL FIXATION SYSTEM

[75] Inventors: Chi-Ming Shih; Tze-Hong Wong; Chen-Dao Shaio, all of Hsinchu; Cheng-Kung Cheng; Chih-Ming Wu, both of Taipei; Wei-Tai Jao, Hsinchu, all of Taiwan

[73] Assignee: Industrial Technology Research Institute, Hsinchu, Taiwan

[21] Appl. No.: 09/245,960

[22] Filed: Feb. 5, 1999

[51] Int. Cl.[7] .................................................. A61B 17/58
[52] U.S. Cl. ................... 606/61; 606/70; 606/71
[58] Field of Search ................... 606/61, 71, 73, 606/75, 70

[56] References Cited

U.S. PATENT DOCUMENTS

| | | | |
|---|---|---|---|
| 5,085,660 | 2/1992 | Lin | 606/73 |
| 5,324,290 | 6/1994 | Zdeblick et al. | 606/61 |
| 5,330,473 | 7/1994 | Howland | 606/61 |
| 5,364,399 | 11/1994 | Lowery et al. | 606/69 |
| 5,620,443 | 4/1997 | Gertzbein et al. | 606/61 |
| 5,702,395 | 12/1997 | Hopf | 606/61 |
| 5,713,900 | 2/1998 | Benzel et al. | 606/61 |
| 5,925,047 | 7/1999 | Errico et al. | 606/61 |

*Primary Examiner*—Michael Buiz
*Assistant Examiner*—Julian W. Woo
*Attorney, Agent, or Firm*—Ladas & Parry

[57] ABSTRACT

An anterior spinal fixation system comprises a pair of equal upper and lower vertebral plate systems and at least two rods arranged in parallel. The upper and lower vertebral plate systems each includes a staple vertebral plate and a universal cover plate which are jointed firmly with each other to retain the ends of the rods. Furthermore, the anterior spinal fixation system of the present invention may also comprise at least one connector plate system retain in the middle of the rods so as to enhance supporting strength and effect of anti-twist.

10 Claims, 4 Drawing Sheets

ANTERIOR SPINAL FIXATION SYSTEM

FIELD OF THE INVENTION

The present invention generally concerns an anterior spinal fixation system adapted to be fixed on the vertebral body of an anterior spine for substituting a damaged vertebral body, supporting the load on a spine, achieving stability of a fractured spine, or recovering from a resection operation for an osteoma spine tumor. The anterior spinal fixation system of the present invention is sufficient in strength, and can be easily assembled and properly positioned in place during a surgical operation. In addition, the present invention further allows the spine to be returned to its normal condition.

BACKGROUND OF THE INVENTION

Accompanied by an increase in traffic injuries, accidents, and the growth of an aging population conditions such as fractures, tumors, degeneration, and aging of the spine are also increasing. Medical treatment and physiotherapy cannot cure most of the patients suffering from these conditions. Therefore, surgical treatment is often needed. During the operation, the fixation systems and instruments are usually required to stabilize and remedy a deformed spine. Essentially, a good spinal implant must meet the following conditions: (1) have good rigidity when assembled; (2) have sufficient stability when fixed to the spine; (3) be adaptable to accommodate spinal deformity, and (4) be easily and safely applied to the spine.

At present, anterior spinal fixation systems are primarily used for burst fractures, spinal tumors, spinal deformities, and degenerative diseases. They should be of low profile and easy for the surgeon to apply.

Clinically, the anterior spinal body is located close to the aorta. This increases the difficulty of performing an anterior surgical operation. Therefore, the use of an anterior spinal fixation systems must have as a primary consideration absolute safety. Another consideration is, to reduce operation time and simplify the operational steps.

U.S. Pat. No. 5,330,473 discloses a connector for a spinal fixation systems, adapted to for connecting two supporting rods. However, it is used to connect the posterior fixation system, not the anterior fixation system.

U.S. Pat. No. 5,620,433, discloses an anterior screw-supporting rod connector, which has upper and lower bolts. This connector cannot be assembled easily.

The Kaneda Device is appreciated by surgeon as one of the best available fixation systems, and is characterized by lateral fixation, including vertebral steel plates, vertebral screws, nuts, supporting rods, and a transverse fixation system. The Kaneda Device allows correction of deformities and provides sufficient rigidity, which is particularly useful when used in operating on spinal fractures, and recovering from a resection spinal tumor operation. However, there is still a need to provide an improved device to resolve the following deficiencies: (1) The Kaneda Device is complicated in use due to its lateral fixation; (2) The laterally-extending supporting rods of the Kaneda Device increase risk during to the operation.

The purpose of the present invention is to resolve the aforesaid deficiencies of the prior art, while at the same time providing an anterior spinal fixation system, which is as the rigid as Kaneda device and also easy to be installed.

SUMMARY OF THE INVENTION

An object of the present invention is to provide an anterior spinal fixation system ("anterior" refers to an implantation position for the fixation system on the spine) which has fewer parts and may be assembled easily. According to this concept, the anterior spinal fixation system generally comprises a pair of similar upper and lower vertebral plate systems and at least two rods, wherein the upper and lower vertebral plate systems respectively retain the ends of the rods.

In a further aspect of the present invention, the vertebral plate systems of the anterior spinal fixation system may be assembled quickly and provide an effective rigidity. Based on this concept, each of the pair of vertebral plate systems is constructed with a universal cover and a staple vertebral plate jointed firmly to each other by locking nuts to retain the rods. Preferably, the universal cover plates of the vertebral plate systems have tapered sides in order to allow the rods to be retained and held tightly between the universal cover plates and the staple vertebral plates.

In a still further aspect of the present invention, the staple vertebral plate of each vertebral plate system is formed diagonally with a pair of through holes for receiving the vertebral screws so as to allow the vertebral plate systems to be mounted to the vertebral body. With the vertebral screws retained under the rods, and in turn the rods retained under the universal cover plate, a tightly retaining structure is obtained.

In an embodiment of the present invention, the anterior spinal fixation system further comprises at least one connector plate system mounted in the middle of the rods to provide additional strength around the middle of the rods, especially for resisting torsion loading. It will be appreciated that the use of the connector plate systems will advantageously reduce the number of rods. Without the connector plate systems, the present invention may still provide the required supporting strength even if the present invention is constructed with only two rods.

Accordingly, system of the present invention is easy to operate because it is assembled in an up-to-down manner, and the rods are also disposed from up to down when assembled. The present invention advantageously reduces the risk of injury during an operation, and also provides the equivalent strength of the Kaneda device.

DETAILED DESCRIPTION OF THE PREFERRED EMBODIMENTS

Figure 1:
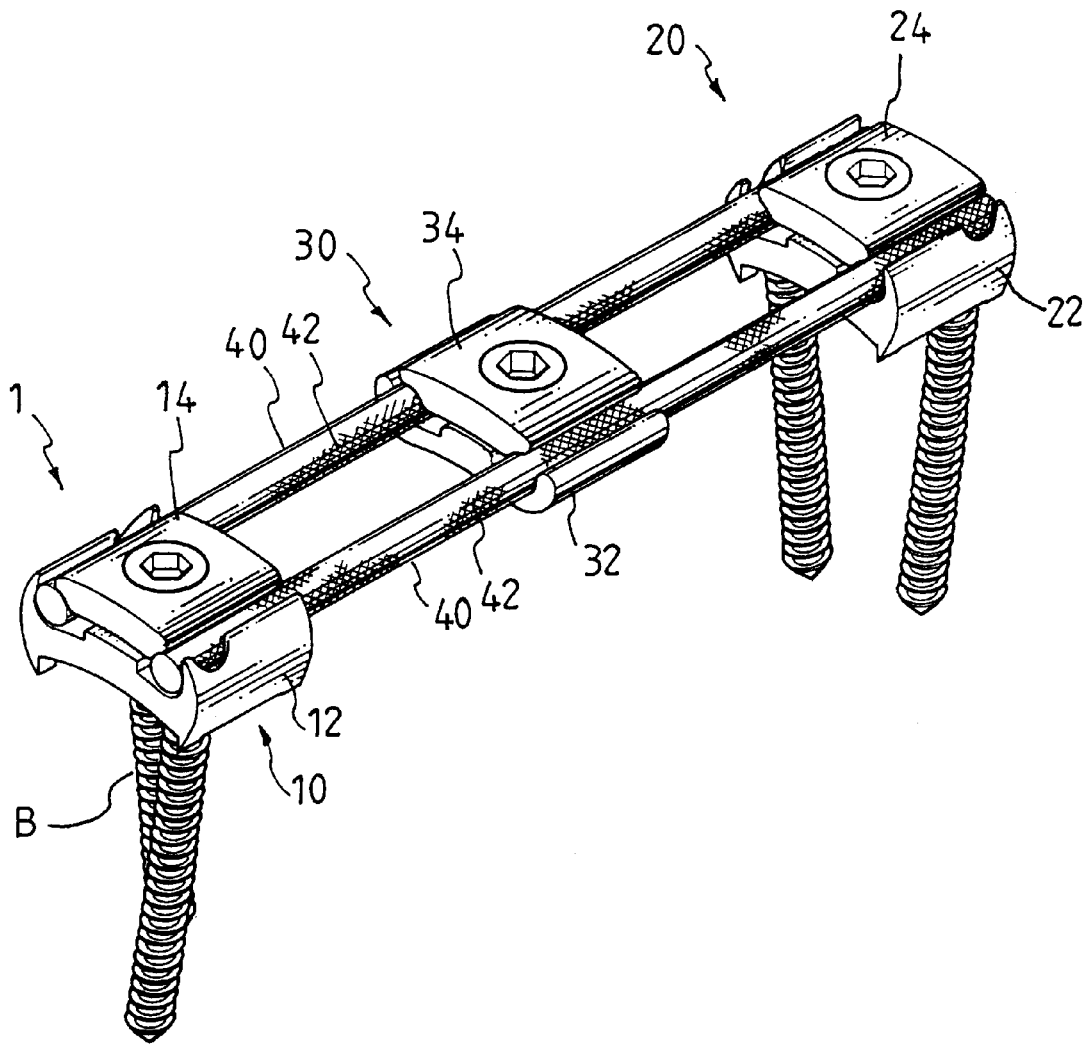
FIG. 1 is a perspective view of an anterior spinal fixation system according to the present invention.

An anterior spinal fixation system (1) according to a preferred embodiment of the present invention is shown in FIG. 1, which essentially consists of a pair of equal upper and lower vertebral plate systems (10,20) and at least two longitudinal rods (40) arranged in parallel. The upper and lower vertebral plate systems (10,20) each includes a staple vertebral plate (12,22) and a universal cover plate (14,24), the universal cover plates being firmly joined to each other by locking nuts (S) to retain the ends of the rods (40), respectively. The rods (40) are known as the fixation rods used in typical spinal fixation system. In a preferred embodiment of the present invention, the rods (40) are formed with knurls on the surfaces thereof, in order to increase frictional retention between the vertebral plate systems (10,20) and the rods (40).

Figure 2:
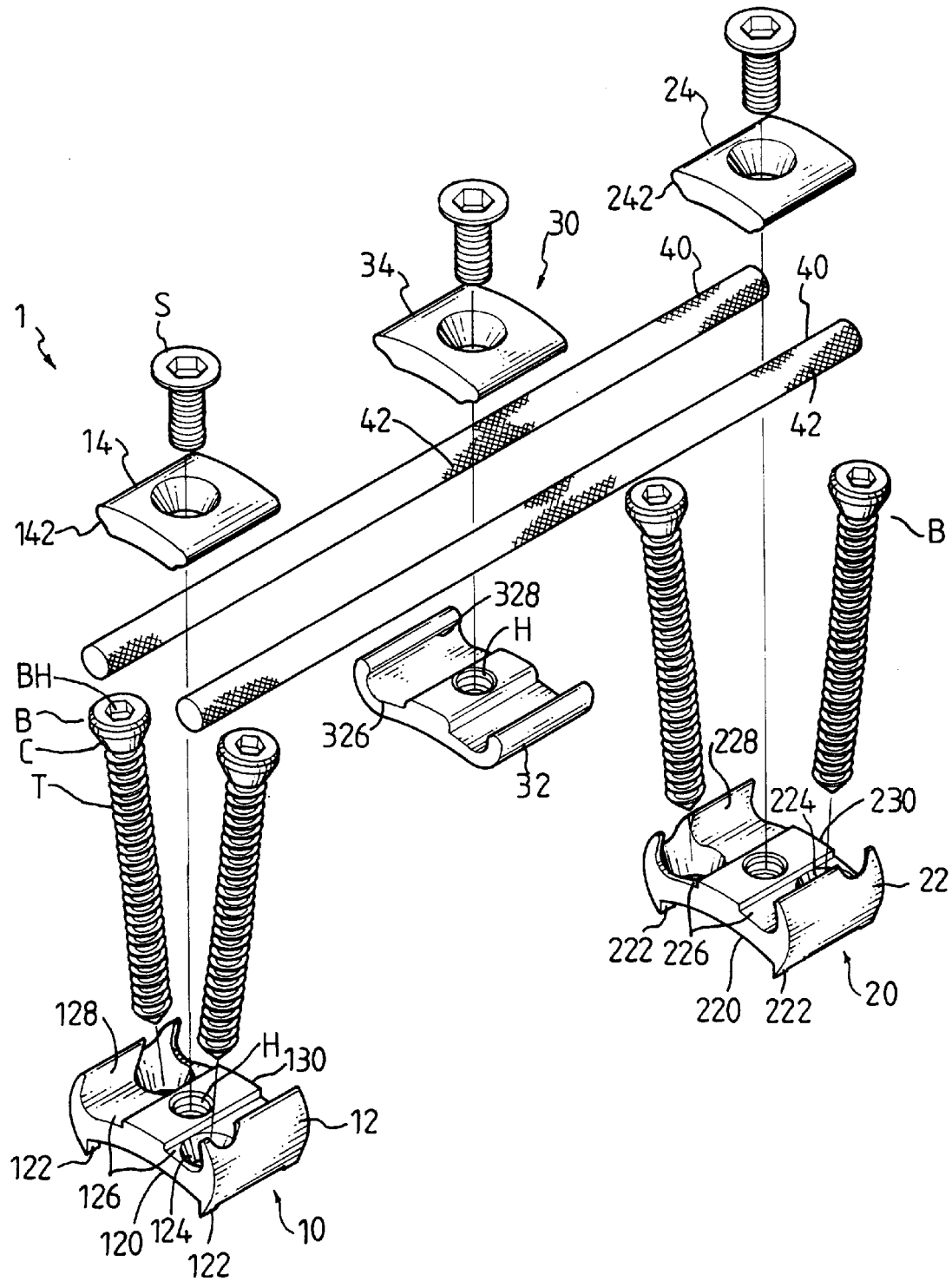
FIG. 2 is an exploded perspective view of the present invention.
Figure 3:
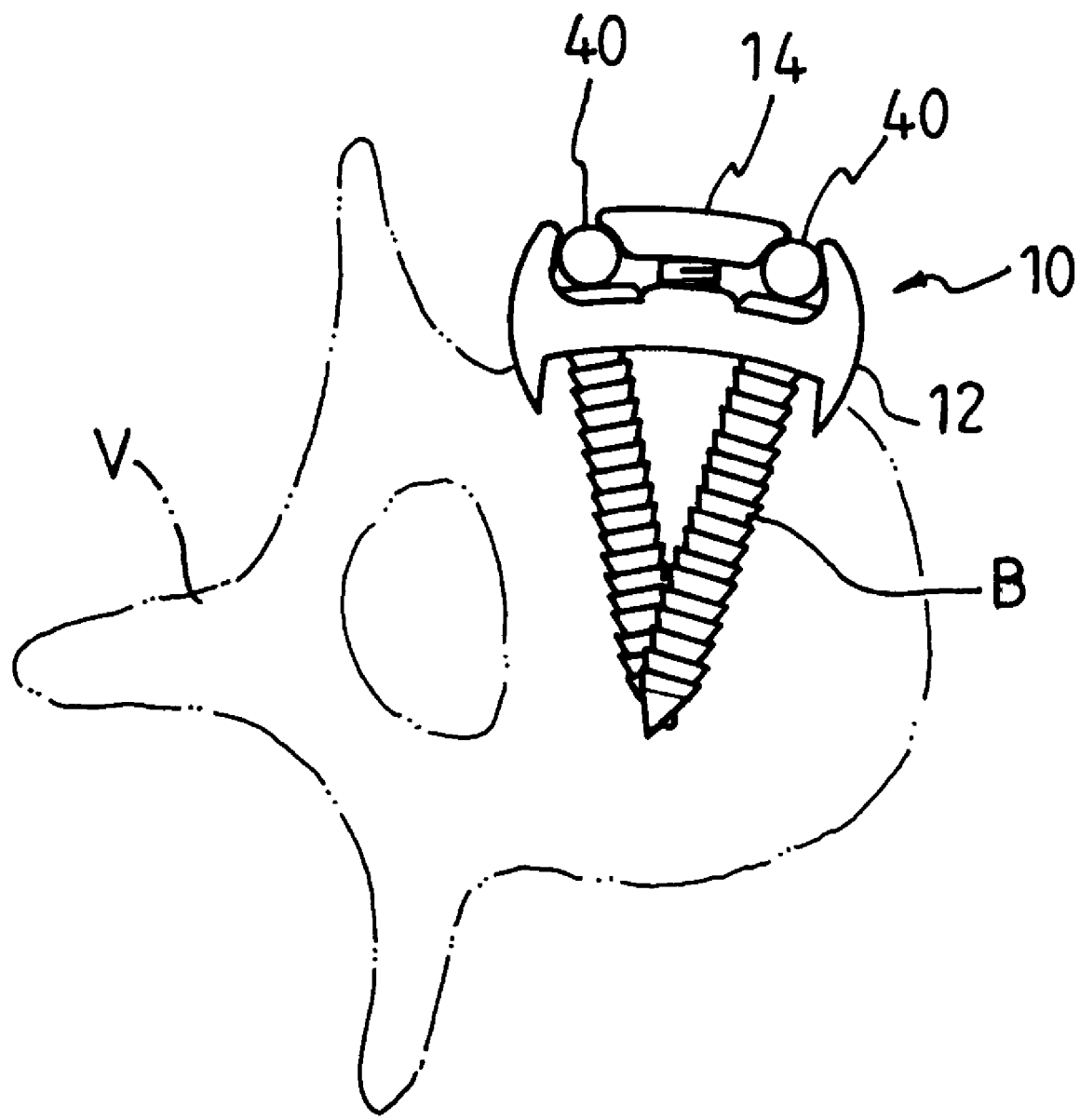
FIG. 3 is a schematic view showing the vertebral plate systems of the invention screwed into a vertebral body by vertebral screws.
Figure 4:
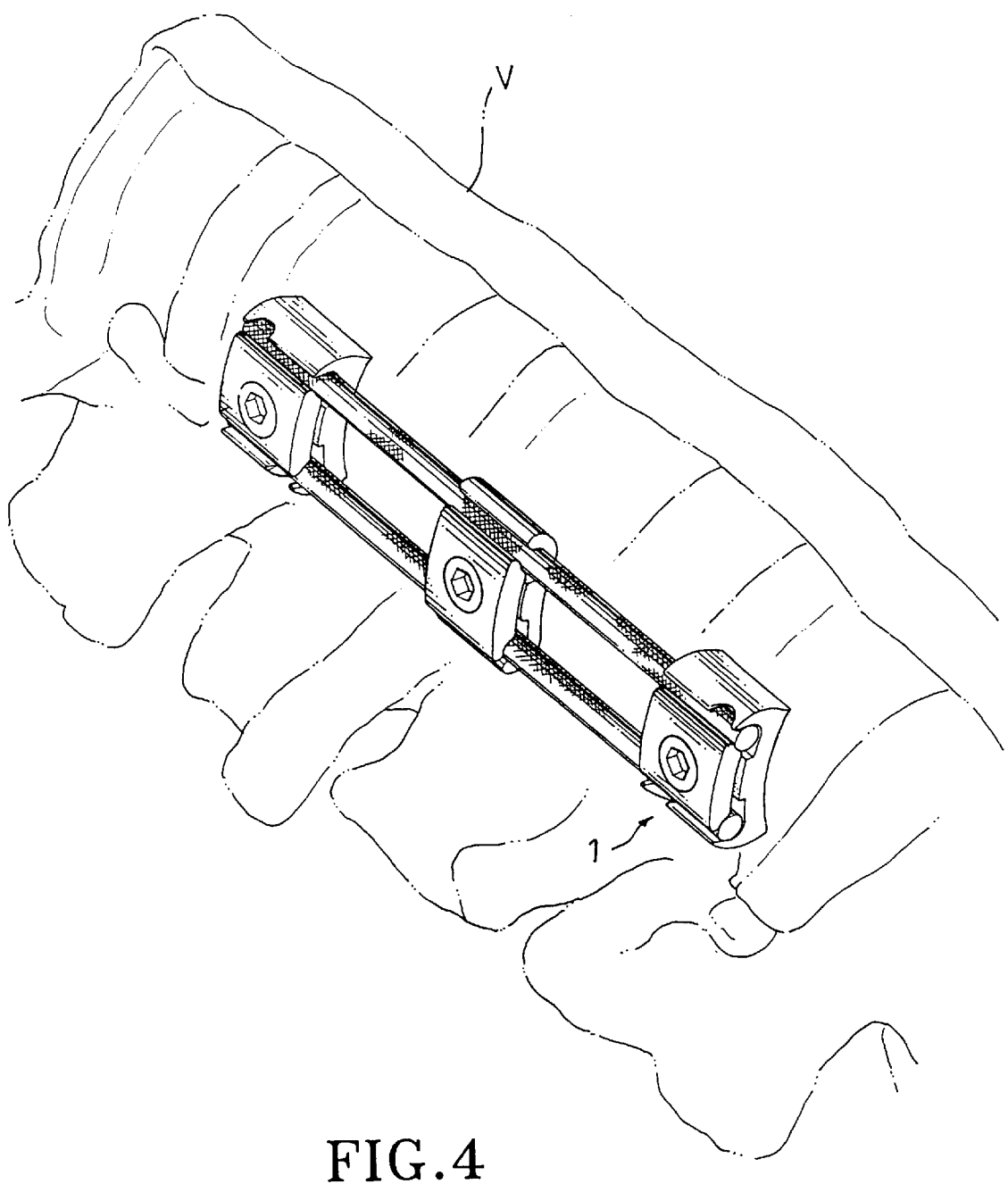
FIG. 4 is a schematic view showing the present invention implanted into the vertebral body.

Referring now to FIGS. 2 and 3, each of the staple vertebral plates (12,22) is provided with a pair of screw holes (124,224) located diagonally at a pair of corners of each staple vertebral plate (12,22). The holes are also inclined with respect to the staple vertebral plates, which allow the vertebral screws (B) to be screwed into the vertebral body (V). The screw holes (124,224) in each of the staple vertebral plates (12,22) are angulated so that then axes do not intersect each other. This prevents interference of the vertebral screws (B) with each other as they are screwed into the vertebral body (V). Screw holes (124,224) preferably have tapered faces, which are downwardly tapered from top surface (130,230). When the vertebral screws (B) are screwed into the vertebral body (V), the tapered faces will engage with conical faces (C) of the vertebral screw heads, so that the vertebral screws (B) are completely recessed in the screws holes (124,224).

The staple vertebral plate (12,22) has a vertebral contact surface (120,220) and a top surface (130,230). The vertebral contact surface (120,220) serves as a contact surface associated with the vertebral body (V), and is laterally curved substantially, and corresponds to the profile of the vertebral body (V). The vertebral contact surface (120,220) further extends downwardly and terminates in a plurality of spikes (122,222) which may be inserted into the vertebral body (V). The top surface (130,230) is for contact surface for the rods (40), and is provided with a plurality of rods channels (126,226) therein to receive the rod (40). Preferably, the outer rims of the rod channels (126,226) further extend upwardly and outwardly to form walls (128,228) to partially embrace the rods, as best shown in FIGS. 2 and 3.

The universal cover plates (14,24) are formed with rod contact surfaces (142,242) preferably tapered downwardly to partially embrace the edges of the rods.

The anterior spinal fixation system (1) preferably further comprises at least a connector plate system (30), which may be mechanically mounted on the rods (40), so as to enhance the supporting strength of the rods (40) as well as prevent twisting of the anterior spinal fixation system (1). Similar to the vertebral plate systems (10,20), the connector plate system (30) also includes a basal connector plate (32) and a universal cover plate (34) firmly joined to each other. The basal connector plate (32) is preferably constructed with rod channels (326) to receive the rods. In one embodiment, the rod channels (326) further include walls (328) to embrace the rod (40) partially. In another aspect, the universal cover plate (34), which has a shape generally similar to that of the universal cover plate (14,24), is preferably formed with a substantially wedged-shape cross-section.

To mount the anterior spinal fixation system (1) onto a damaged vertebral body (V), it is necessary to tap the staple vertebral plate (12,22) slight with an instrument until the spikes (122,222) penetrate into the vertebral body (V). After the staple vertebral plates (12,22) are completely installed on the vertebral body (V), the vertebral screws (B), are then installed the rods (40), and finally the universal cover plates (14,24) and the connector plate system (30). The required wire set up number of the connector plate systems (30) may vary depending on the required supporting strength. Due to the wedge profile of the cross-section of the universal cover plate (14,24), the rods (40) will tightly and naturally be retained between the rod contact surfaces (142,242) and the walls (128,228), especially when the staple vertebral plate (12,22) and the universal cover plate (14,24) are tightly secured together by the locking nuts.

It will be appreciated that the vertebral screws, the vertebral plate systems, and the rods employed in the present invention are installed or set up in an up-to-down manner. And the rods may also be loosened or tightened by adjusting the span between the upper and the lower pairs of vertebrae screws. This is very convenient to remedy a damaged vertebral. Overall, the present invention not only helps to reduce the time spent on the system installation and the area of wound, it also reduces the probability affect of adversely affecting adjacent membranes and issue during the operation, thus making it easier for the damaged vertebral to recover and return to its normal position. These features cannot be attained by the existing fixation systems. In addition, diseases related to lateral deformity may also be remedied by the present invention.

The anterior spinal fixation system of the invention is particularly suitable for fixing an unstable vertebrae and providing complete or partial function of a spine is seriously damaged, deformed, or degenerated. To operate the present invention, first of all, it is necessary to select appropriate positioning plates and implant the plates into the upper and the lower bodies of a damaged or pathological vertebral body. After adjusting for an adequate span between the upper and the lower pairs of the vertebral screws, the vertebral screws tightly engaged and press the universal cover plates against the rods by using the locking nuts in order to provide an initially secured and rigid condition. The fixation system and the vertebral body are integrated as an unit and a stabilizing is achieved. Therefore, the fusion rate of the vertebral body will be enhanced when a bone graft is performed.

While the invention has been particularly described with respect to preferred embodiments thereof, it will be understood by those skilled in the art that the above and other changes in form and detail may be made without departing from the scope and spirit of the invention.

What is claimed is:

1. An anterior spinal fixation system, comprising:
a pair of identical upper and lower vertebral plate systems and at least two rods arranged in parallel, said upper and lower vertebral plate systems each including a staple vertebral plate and a universal cover plate joined firmly with each other to cooperatively retain ends of said rods; wherein said staple vertebral plate has a vertebral contact surface for engaging a vertebral body and a top surface engaged with the rods; said vertebral contact surface having a laterally and downwardly extending slightly curved profile terminating in a plurality of spikes, said top surface having a plurality of rod channels for receiving said rods.

2. The anterior spinal fixation system of claim 1, wherein each of the said rods has a knurl-like surface.

3. The anterior spinal fixation system of claim 1, wherein each said staple vertebral plate has screw holes located diagonally at either pair of corners of said staple vertebral plate and extending through said staple vertebral plate.

4. The anterior spinal fixation system of claim 3, wherein each of said screw holes in said staple vertebral plate is inclined with respect to said staple vertebral plate, and wherein said screw holes are angulated so that axes of said screw holes do not intersect each other.

5. The anterior spinal fixation system of claim 3, wherein each said screw hole is formed at said top surface so that the respective screw can be recessed in the vertebral plate.

6. The anterior spinal fixation system of claim 1, wherein said rod channels have outer rims extending upwardly to form walls to partially embrace said rods.

7. The anterior spinal fixation system of claim 6, wherein each said universal cover plate has sides which taper downwardly and inwardly for contact with the ends of the respective rods.

8. The anterior spinal fixation system of claim 1, further comprising at least one connector plate system retained at a middle of said rods, said connector plate system including a basal corrector plate and a universal cover plate firmly secured to each other, said basal corrector plate being provided with rod channels for receiving said rods.

9. The anterior spinal fixation system of claim 8, wherein said rod channels in said basal corrector plate have outer rims extending upwardly to form walls for embracing said rods.

10. The anterior spinal fixation system of claim 9, wherein said universal cover plate of said connector plate system has sides which taper downwardly and inwardly for contact with said rods.

* * * * *